United States Patent [19]

Aguadisch et al.

[11] Patent Number: 5,788,977
[45] Date of Patent: Aug. 4, 1998

[54] METHOD OF MAKING CONTROLLED RELEASE DEVICES

[75] Inventors: Louis Aguadisch, Valbonne; Magali Barbaroux, Cannes, both of France; Frederic Dalle, Kraainem, Belgium

[73] Assignee: Dow Corning France S.A., Sophia Antipolis, France

[21] Appl. No.: 803,739

[22] Filed: Feb. 21, 1997

[30] Foreign Application Priority Data

Feb. 23, 1996 [FR] France ..................... 96 02267

[51] Int. Cl.$^6$ ..................................................... A61F 13/00
[52] U.S. Cl. ..................... 424/422; 424/424; 424/425; 424/430; 424/432
[58] Field of Search ..................... 424/422, 424, 424/425, 430, 432

[56] References Cited

U.S. PATENT DOCUMENTS

| 4,300,557 | 11/1981 | Refojo et al. | 424/424 |
| 4,304,226 | 12/1981 | Drobish et al. | 128/832 |
| 4,888,074 | 12/1989 | Pocknell | 156/217 |
| 5,614,212 | 3/1997 | D'Angelo | 424/449 |

FOREIGN PATENT DOCUMENTS

| 0 153 825 | 4/1985 | European Pat. Off. . |
| 93 21902 | 11/1993 | WIPO . |

*Primary Examiner*—D. Gabrielle Brouillette
*Attorney, Agent, or Firm*—Richard I. Gearhart

[57] ABSTRACT

A process is disclosed for making devices which release active material, e.g. a drug, at a controlled rate, which device comprises a closed container and the active material. The device is made by first making a hollow envelope, e.g. by extrusion or moulding, followed by introducing the active material into the void of the envelope. The device may have a ring or cylindrical form.

8 Claims, 1 Drawing Sheet

METHOD OF MAKING CONTROLLED RELEASE DEVICES

This invention is concerned with controlled release devices and methods of making them.

Numerous devices have been proposed for the controlled release of drugs to the human or animal body. For example, it has been proposed to manufacture a controlled release drug delivery device by use of a tube of cured silicone rubber by sealing one end with a curable silicone composition, charging a drug-containing composition into the tube, sealing the open end of the tube with a curable silicone composition and then curing the composition.

Whilst devices made in this way are efficacious as drug delivery vehicles, they require several steps in their manufacture and require the use of a prolonged cure time, which requires significant expenditure of time and effort. Also, the curing reaction required to cure the silicone is generally a hydrosilylation which is a reaction susceptible of corruption or severe inhibition in the presence of certain chemical groupings which are desirable in some drugs. The possibility to overcome retardation of the cure by heating is often not realistic as the drug materials may be adversely affected by heating to temperatures in excess of about 25° C.

We have now found that one may prepare controlled release devices efficiently and in a controlled manner by first forming a hollow envelope and then introducing the drug into the envelope in a dosed amount.

In a preferred embodiment, we have found that one may prepare controlled release devices efficiently and in a controlled manner by first forming a hollow envelope using a curable silicone based composition material, curing the envelope and then introducing the drug to the envelope in dosed amount.

The present invention provides in one of its aspects a method of making a device capable of releasing an active material at a controlled rate, which device comprises a closed container inside which is located the active material and which container has walls which are permeable to the active material, which method comprises forming a closed container having an empty space therein and introducing an active material into the empty space within the closed container.

In a preferred embodiment, at least a portion of the envelope is formed from a silicone based composition and the silicone composition is cured prior to introducing the active material.

The composition used to form the envelope can be any which are recognised as suitable for insertion or implantation in the human or animal body, for example polymers and copolymers of unsaturated monomers (e.g., polymethacrylates, polyvinyl chloride, polyethylene, polyacrylonitrile, polyvinyl acetate, polybutadiene) polyesters, polyamides, polyurethanes, cellulose esters and silicones. Examples of preferred materials include the silicone materials commonly used for controlled release drug delivery devices. In a more preferred method we prefer to employ one or more silicone compositions to provide the whole of the envelope.

The composition may be formulated so that in use of the device it serves to permit transfer of the active ingredient from the device, for example by way of diffusion, via micropores or by osmosis. Thus, one may employ a material which is permeable to body fluids or one which is not.

Suitable compositions include but are not limited to those which are flowable liquids at room temperature or elevated temperature and which are suitable for processing in conventional moulding or extrusion machinery designed for moulding plastics material by injection moulding, blow moulding, roto-moulding, fusible core moulding or other techniques. They are also preferably curable materials or materials which harden on cooling so that they retain their shape, i.e., they are resistant to flow after moulding and before cross linking has fully developed.

The composition preferably comprises an organo silicon compound capable of use as a hot melt or more preferably capable of crosslinking with or without the presence of crosslinking agents so that it is curable to a shape retaining and preferably elastomeric state. Such crosslinking may be performed at ambient temperatures or at elevated temperatures preferably of the order of up to 210° C. Elastomer forming silicone compounds comprising organopolysiloxanes having silicon-bonded hydroxyl groups which may be crosslinked to elastomers by the addition of a crosslinking agent and a condensation catalyst may be used. In such compounds, the organopolysiloxane is generally a polydiorganosiloxane having terminal silanol groups. The crosslinking agent may be for example an alkoxy silane or an alkyl polysilicate e.g., methyl trimethoxysilane or ethyl polysilicate, or it may be an alkyl hydrogen polysiloxane e.g., a polymethylhydrogensiloxane. A variety of catalysts may be employed, the organic metal compounds e.g., stannous octoate, dibutyltin. dilaurate, alkyl titanates and titanium chelates being illustrative of these.

Such elastomer-forming compounds are well known in the art and have been described in for example British Patent Numbers: 841 825 128 957 255 and 962 061.

Preferred elastomer-forming silicone compositions are those which crosslink, for example upon heating, without production of volatile by-products. Among the benefits of using the preferred materials, the absence of volatile by-products ensures absence of undesirable voids in the moulding and permits use of a simple manufacturing process. Compositions which crosslink through a free radical mechanism when irradiated or heated may be used.

The most preferred compositions are those silicone compositions which crosslink through a hydrosilylation reaction and which comprise one or more organopolysiloxanes having per molecule at least two silicon-bonded groups having aliphatic unsaturation, one or more organosilicon compounds having at least two silicon-bonded hydrogen atoms and a catalyst e.g., a noble metal such as a platinum compound or complex which promotes the reaction between unsaturated groups and silicon-bonded hydrogen atoms. The aliphatically unsaturated groups are preferably olefinically unsaturated. The organopolysiloxane used in such a composition typically is a high molecular weight polysiloxane and comprises units of the general formula $Q_aQ'SiO_{(3-a)/2}$ and $Q_bSiO_{(4-b)/2}$ wherein Q denotes a monovalent hydrocarbon or substituted hydrocarbon group having no more than 8 carbon atoms, for example a methyl or a phenyl group, Q'denotes an organic group having olefinic unsaturation, preferably being a vinyl, allyl or hexenyl group. Preferably, at least 80% of the silicon-bonded substituents other than the unsaturated organic groups are methyl. a has a value of 1 or 2 and b has a value of 0, 1, 2 or 3.

The organosilicon compound used in such a composition is typically an organohydrogensiloxane having a viscosity up to about 50 mm²/s and having at least two silicon-bonded hydrogen atoms per molecule and the remaining silicon-bonded substituents being monovalent hydrocarbon groups having no more than 8 carbon atoms, preferably being methyl groups. The platinum containing compound or complex may be, for example, chloroplatinic acid, platinum acetonylacetonate or a complex of platinous halides with unsaturated compounds such as ethylene, propylene, organovinylsiloxanes or styrene.

The composition may and preferably does include a catalyst inhibitor, for example an alkynyl compound such as an acetylenically unsaturated secondary or tertiary alcohol for example ethynyl cyclohexanol. The preferred compositions comprise a silicone composition designed to have a "working time" adequate to permit the moulding process to be carried out and capable of full cure with elimination of volatiles by heating preferably to a temperature in the range of up to 200° C. Compositions of this type are well known in the art and are commercially available.

The composition may and preferably does include a finely divided filler. For example, the compositions will normally contain one or more finely divided, reinforcing or extending fillers such as high surface area fume and precipitated silicas, crushed quartz, diatomaceous earths, calcium carbonate, barium sulphate, iron oxide, titanium dioxide and carbon black. The proportion of such fillers employed will depend on the properties desired in the elastomer-forming composition and the cured elastomer. Usually the filler content of the composition will reside within the range from about 5 to about 100 parts by weight per 100 parts by weight of polymer.

By the expression "active material" as used herein is meant an agent essential or contributing to life support or nutrition of living organisms and especially therapeutic or diagnostic agents suitable for use in treatments of the human or animal body. Examples of such materials include those which are intended to be released into body fluids by diffusion or osmosis, for example, via the blood stream or the gastrointestinal tract. They may be hydrophilic or lipophilic organic or inorganic materials which are pharmaceutically active materials and can usefully be administered, for example, over a long period of time. The active ingredient may be chosen in accordance with normal pharmaceutical practice and will normally have a pH appropriate to the conditions at the region in the body where it is to be released. If appropriate, the pH of the substance may be buffered in order to preserve its activity. Therapeutic agents which may be employed include, for example, organic and inorganic drugs which act on the central nervous system, contraceptive, hormonal replacement, cardiovascular and ophthalmic drugs and antiparasitic, antibacterial, antifungal and antiviral agents.

The invention is preferably employed to provide a hollow envelope consisting entirely of silicone material by a moulding process. The envelope may have any desired shape or configuration for example a cylinder or a ring. One preferred form is a ring for vaginal use. Furthermore, the envelope may enclose more than one void or hollow compartment so that different active materials may be introduced to them to be dispensed from the one device. Alternatively, the envelope may have a sequence of interconnected compartments containing active material or excipient formulated to generate osmotic pressure in the compartments containing excipient whereby to boost the bursting release of the active material from the envelope.

In one preferred form the cured hollow envelope is formed with an integral septum capable of being pierced by a hypodermic needle and of self-sealing upon removal of the needle so that the active material may be introduced to the cured envelope as a liquid via a needle. It is also possible to introduce the active material via injection into the hollow chamber when the active material is liquid when injected and subsequently forms a solid or gel like material, e.g. by cooling, crosslinking or other forms of solidification. A similar approach is possible if the injected material is thixotropic. In such case it is not necessary to inject the active material through a self-sealing septum. In another preferred form a slit is formed in the cured envelope through which the active material may be introduced to the cured envelope for example as a powder or a solid.

The concentration of the active e.g. therapeutic agent employed, the volume of the device and the size of its surrounding sheath, are selected to provide the required release rate of the active ingredient or ingredients and the required useful lifetime of the device, i.e., the time that the device will be capable of releasing the active ingredient at the required rate.

By use of a method according to the invention it is possible to manufacture an envelope of cured material which can be sterilised and from which all volatile materials have been removed before introduction of the active material therein and one may then introduce an active material without any concern as to whether it will be adversely affected by the heating in a subsequent production step or as to whether it will interfere with the curing of the silicone.

There now follows a description to be read with the accompanying drawings of a method according to the inventions and the products thereof. All parts are by weight unless the context otherwise requires and all viscosity measurements were made at 25° C.

Figure 1:
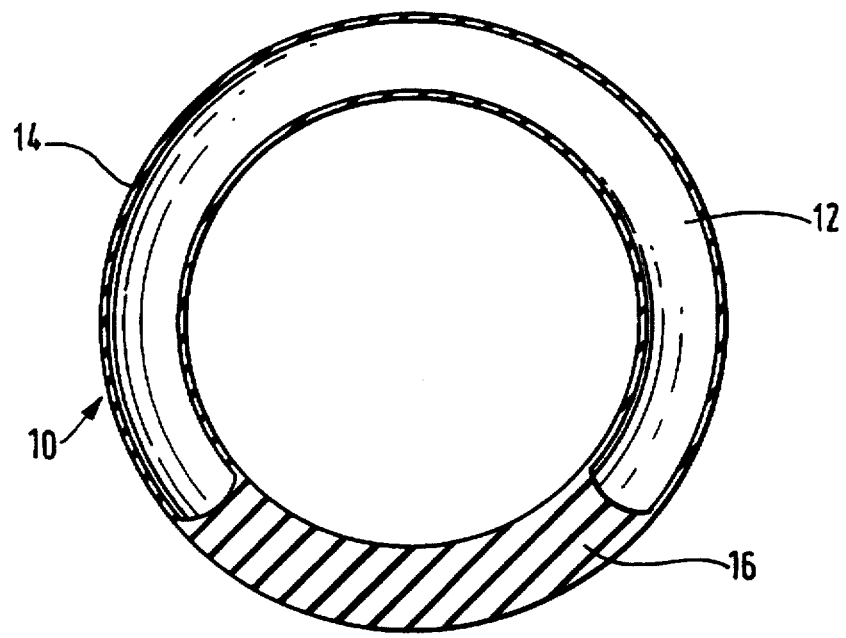
FIG. 1 is a sectional view of a ring device.
Figure 2:
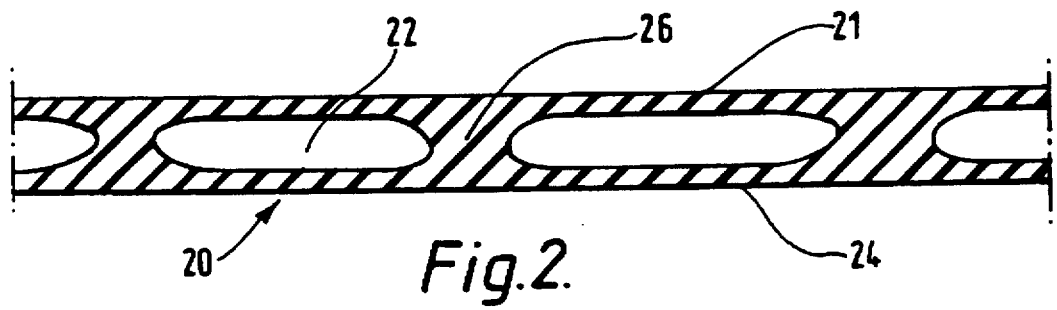
FIG. 2 is a sectional view of a thread of hollow implants.

The ring device was prepared from a first composition formed by mixing a curable medical grade elastomer comprising two parts A and B. The part A comprised 95 parts by weight of an α,ωvinyldimethyl siloxane polydimethyl siloxane having an average viscosity of 450 mpa.s, 4.4 parts by weight of a silica and 0.5 parts by weight of a platinum complex catalyst. Part B contains 78 parts by weight of the above mentioned polydimethyl siloxane and 22 parts by weight of a methyl hydrogen siloxane dimethyl siloxane copolymer. Parts A and B are mixed in a 10/2 weight ratio, of which 2.4 parts were injected into a toric mould using a syringe. The mould was rotated about its inner axis to cause the mixture to flow and coat the whole inner surface of the mould. The mould was then allowed to remain stationary and silicone material allowed to flow down to collect in the lower portion of the mould to bridge the void within the mould as at (16). The material was allowed to cure at room temperature. No material was lost from the mould during this curing step. The hollow ring (10) so formed was removed from the mould by separating two halves of the mould. The ring (10) so formed comprised an annular envelope (14) of silicone elastomer enclosing a part-circular ring-like void (12) or hollow compartment. A single plug or septum (16) of cured silicone elastomer extends across the thickness of the ring.

An active material was charged to the void from a hypodermic needle (18) inserted through the septum (16) and into the void (12). After charging the active material to the void the needle was removed, allowing the septum (16) to seal itself.

The thread of hollow implants was formed by use of a second composition comprising two parts, A and B. The part A comprised 70 parts of a dimethyl vinyl siloxy end blocked polydimethylsiloxane having a viscosity of about 2,100 mm²/s, 30 parts of hexamethyldisilazane treated silica and 0.9 parts of the platinum catalyst. The part B comprised 88 parts of the dimethyl vinyl siloxy end blocked polydimethylsiloxane having a viscosity of about 2,100 mm²/s, and 12 parts of the polydimethyl methylhydrogen siloxane. 10 parts of the part A were mixed with 2 parts of the part B at room temperature and then degassed and introduced to a syringe. Sufficient of the silicone from the syringe was introduced to the mould to occupy 50% of the volume of a mould consisting of a standard 2 ml plastic pipette, 25 cm long. The silicone coated the mould surface as it entered the mould. 0.1 ml of air was injected into the mould to pressurise the silicone. 0.01 parts of the silicone was then injected into the mould followed by injection of 0.1 ml of air. This sequence was repeated seriatim to fill the mould. The silicone composition was allowed to cure at room temperature to form an elastomer. Upon demoulding, a silicone elastomer thread (20) was recovered from the mould having alternate hollow sections (21) approximately 28 mm long enclosing a void (22) within a wall (24) of a thickness of about 350 μm separated by plugs (26) of silicone about 20 mm long. An active material was charged to each void from a hypodermic needle inserted through the plug (26) and into the void (22). After charging the active material to the void the needle was removed, allowing the plug (26) to seal itself.

That which is claimed is:

1. A method of making a device which releases an active material suitable for treating the human or animal body at a controlled rate comprising:

forming a closed hollow envelope having an empty space therein from an uncured silicone containing material;

curing said closed hollow envelope, said closed container being permeable to the active material; and introducing an active material into the empty space of the closed hollow envelope.

2. The method of claim 1 wherein the closed hollow envelope is formed by a molding process.

3. The method of claim 1 wherein the closed hollow envelope is formed with an integral septum.

4. The method of claim 3 wherein the active material is introduced into the closed hollow envelope by inserting a needle through the septum and injecting the active material in liquid form through the needle.

5. The method of claim 1 wherein the active material is introduced into the closed hollow envelope in a solid form.

6. The method of claim 5 wherein a slit is formed in the closed hollow envelope and the active material is introduced through the slit.

7. The method of claim 1 wherein the device contains more than one closed hollow envelope.

8. The method of claim 7 wherein different active materials are introduced to each of the closed hollow envelopes.

* * * * *